United States Patent [19]

Cohen et al.

[11] Patent Number: 4,610,259

[45] Date of Patent: Sep. 9, 1986

[54] EEG SIGNAL ANALYSIS SYSTEM

[75] Inventors: Daniel E. Cohen, Eden Prairie; Frederick T. Strobl, Chaska, both of Minn.

[73] Assignee: CNS, Inc., Eden Prairie, Minn.

[21] Appl. No.: 527,955

[22] Filed: Aug. 31, 1983

[51] Int. Cl.$^4$ ............................................. A61B 5/04
[52] U.S. Cl. .................................................. 128/731
[58] Field of Search ........................................ 128/731

[56] References Cited

U.S. PATENT DOCUMENTS

| | | | |
|---|---|---|---|
| 3,495,077 | 2/1970 | Hiltz et al. | 128/731 X |
| 4,171,696 | 10/1979 | John | 128/731 |
| 4,188,956 | 2/1980 | John | 128/731 |
| 4,201,224 | 5/1980 | John | 128/731 |
| 4,216,781 | 8/1980 | John | 128/731 |
| 4,279,258 | 7/1981 | John | 128/731 |
| 4,407,299 | 10/1983 | Culver | 128/731 |
| 4,408,616 | 10/1983 | Duffy et al. | 128/731 |
| 4,411,273 | 10/1983 | John | 128/731 |
| 4,412,547 | 11/1983 | Callahan et al. | 128/731 |
| 4,493,327 | 1/1985 | Bergelson et al. | 128/731 X |

*Primary Examiner*—Donald R. Valentine
*Attorney, Agent, or Firm*—Kinney & Lange

[57] ABSTRACT

An electroencephalograph (EEG) signal analyzer allows the examination of the changes in EEG cerebral activity at various sites in response to an event (e.g. a stimulus or task). The analyzer includes one or more signal processing modules which periodically sample the EEG signal from each of the sites, convert the sampled signals to digital sample values, and store those values. Digitized waveforms based on the stored digital sample values and having a length equal to or greater than the period of the lowest frequency of interest are transformed from the time to the frequency domain. For each of a plurality of epochs, a frequency spectrum is produced having frequency content which has a content uniquely due to the digital sample values from that epoch. A weighted means frequency value for each site during each epoch is derived from the corresponding frequency spectrum. Based upon the weighted mean frequency values, output signals are provided to a display and a printer to produce graphical representations of cerebral activity with time at the various sites in response to the event.

24 Claims, 11 Drawing Figures

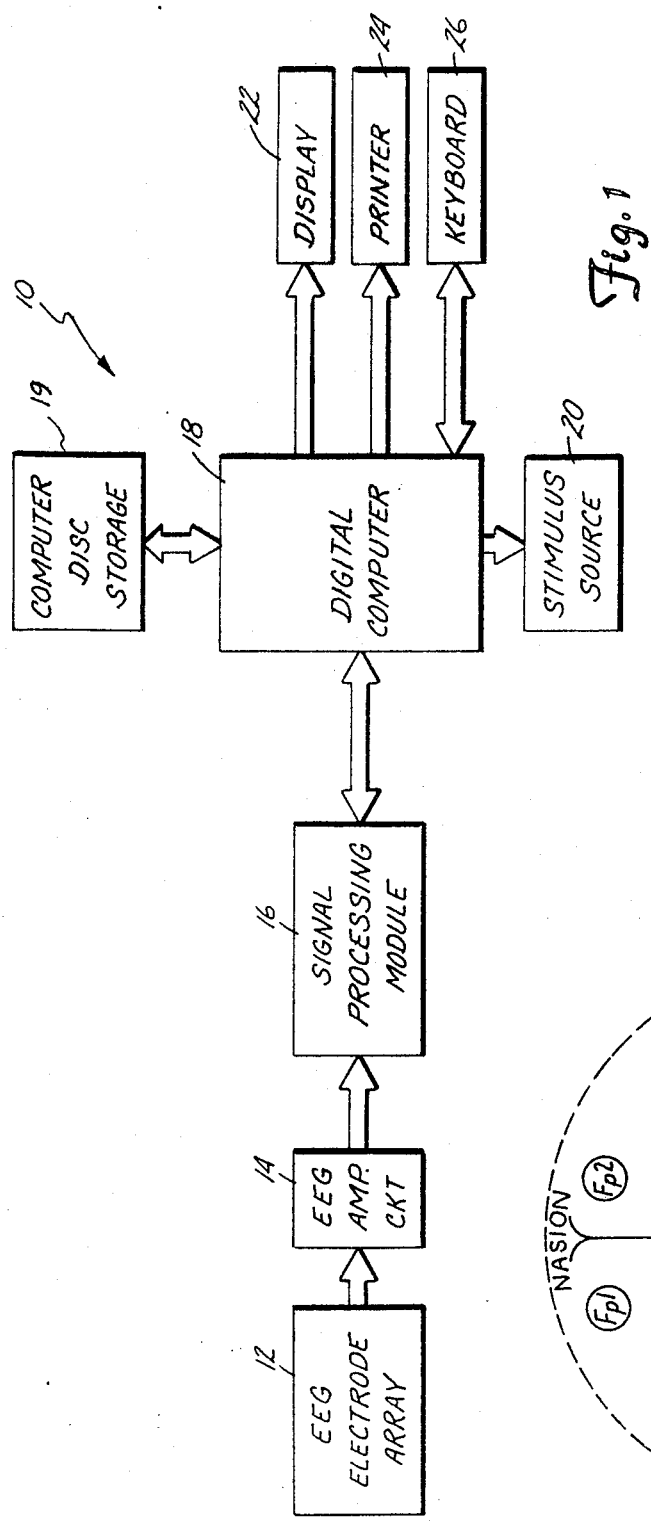
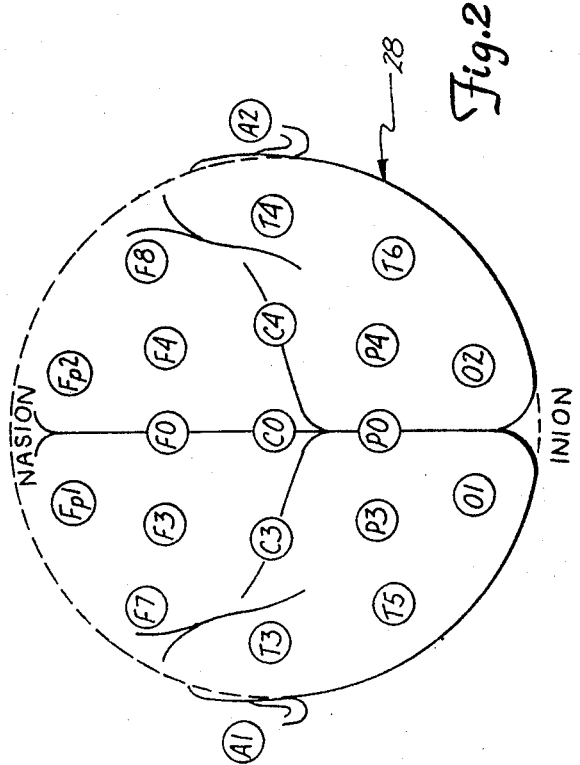

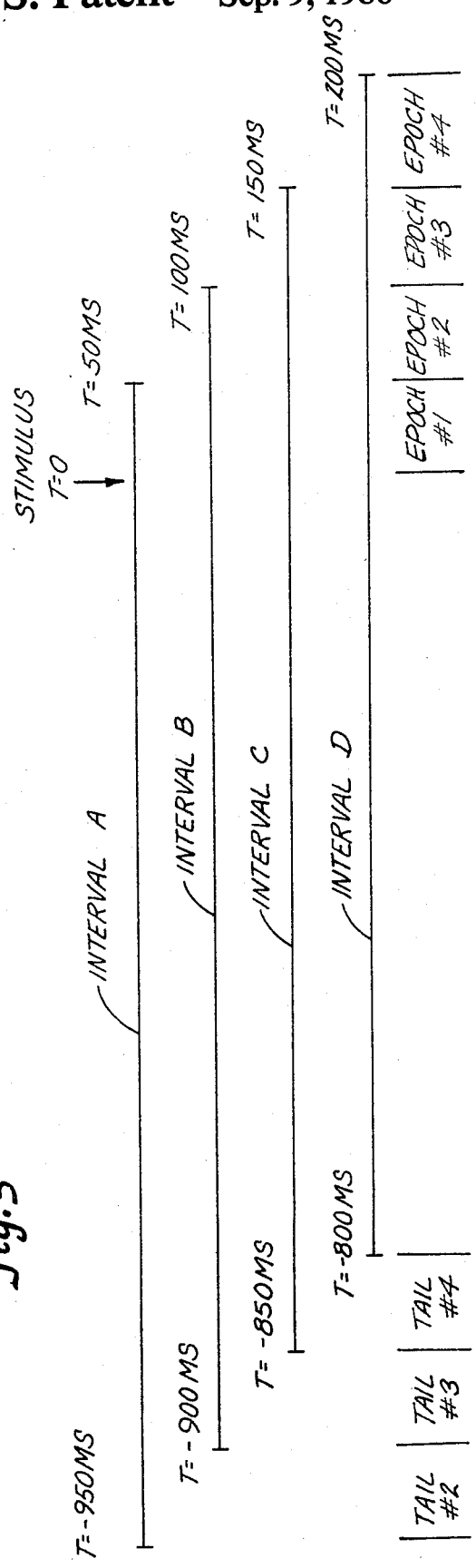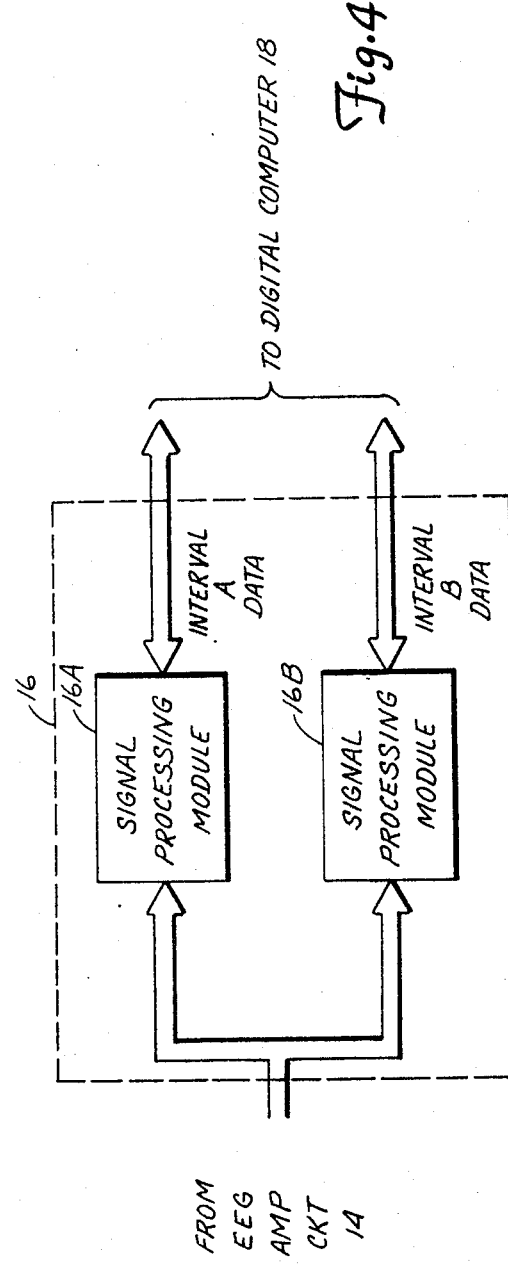

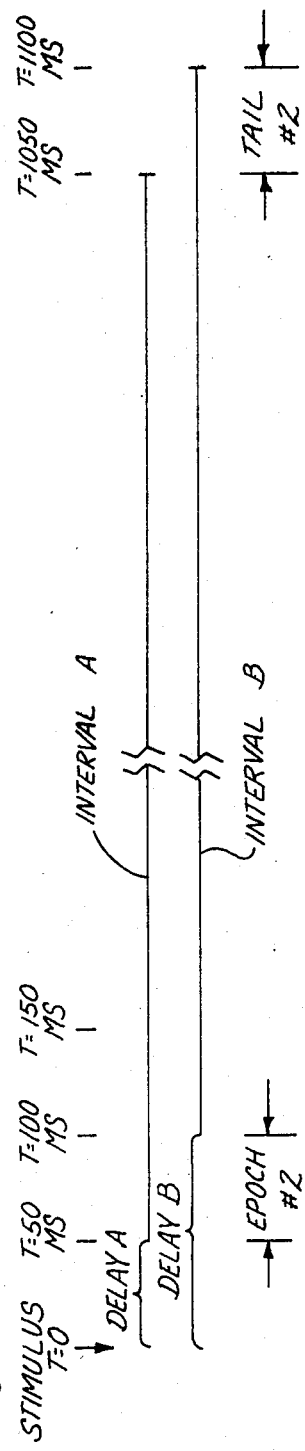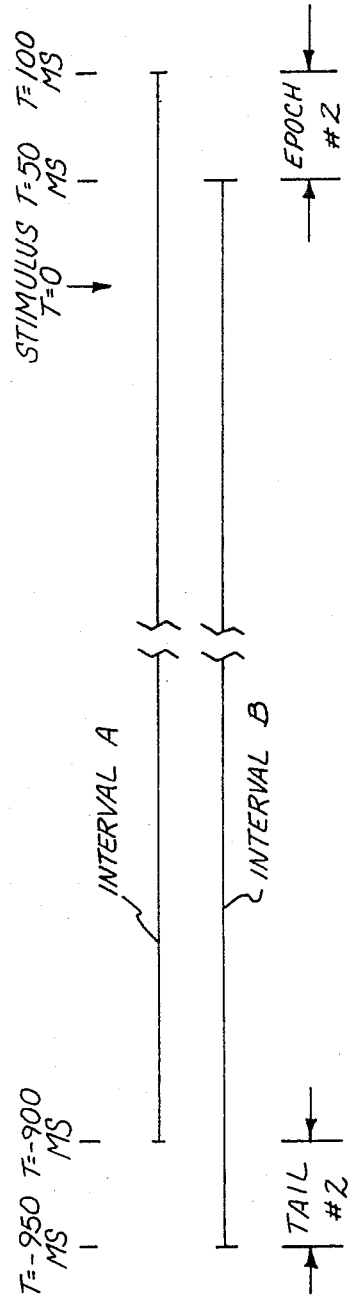

Fig. 8

ADJUSTED FREQUENCY VALUES

| 0→50 | 50→100 | 100→150 | 150→200 | 200→250 | 250→300 | 300→350 | 350→400 | 400→450 | 450→500 | 500→550 | 550→600 | 600→650 | 650→700 | 700→750 | 750→800 |
|---|---|---|---|---|---|---|---|---|---|---|---|---|---|---|---|
| C3 | O2 | FP1 | F7 | T6 | F3 | FP2 | O1 | F7 | F4 | | | | | | |
| O2 | P4 | FP2 | T4 | FP2 | O1 | F7 | T5 | FP1 | T4 | | | | | | |
| F3 | F8 | C3 | T6 | F7 | C4 | O1 | P3 | T3 | F8 | | | | | | |
| P3 | T3 | F3 | FP2 | F8 | F4 | P4 | T3 | F8 | FP2 | | | | | | |
| C4 | T6 | T4 | F3 | T4 | P3 | P3 | FP1 | F4 | T6 | | | | | | |
| P4 | C3 | O2 | FP1 | FP1 | C3 | T5 | C4 | C1 | F7 | | | | | | |
| O1 | FP2 | T5 | T5 | P3 | P4 | FP1 | T6 | P3 | C3 | | | | | | |
| F4 | C4 | F4 | T3 | T5 | FP1 | T3 | P4 | F3 | T5 | | | | | | |
| T4 | T5 | F8 | C4 | O1 | T5 | T4 | O2 | T6 | O2 | | | | | | |
| F8 | F7 | P4 | P4 | C3 | T6 | C4 | C3 | T5 | C4 | | | | | | |
| F7 | O1 | O1 | F4 | C4 | T3 | F3 | F3 | T4 | P4 | | | | | | |
| FP2 | F3 | P3 | F8 | T3 | F7 | F4 | T4 | FP2 | T3 | | | | | | |
| FP1 | P3 | T3 | O2 | F3 | O2 | F8 | F4 | O2 | F3 | | | | | | |
| T5 | F4 | T6 | O1 | O2 | F8 | C3 | F8 | C4 | FP1 | | | | | | |
| T6 | T4 | C4 | C3 | P4 | T4 | O2 | FP2 | P4 | O1 | | | | | | |
| T3 | FP1 | F7 | P3 | F4 | FP2 | T6 | F7 | C8 | P2 | | | | | | |

WEIGHTED MEAN FREQUENCY VALUES

| 0→50 | 50→100 | 100→150 | 150→200 | 200→250 | 250→300 | 300→350 | 350→400 | 400→450 | 450→500 | 500→550 | 550→600 | 600→650 | 650→700 | 700→750 | 750→800 |
|---|---|---|---|---|---|---|---|---|---|---|---|---|---|---|---|
| O2 | O2 | O1 | T6 | T6 | O1 | O1 | O1 | O1 | T6 | | | | | | |
| O1 | T6 | O2 | O1 | O1 | F3 | O2 | T6 | T6 | O2 | | | | | | |
| C3 | O1 | C3 | O2 | O2 | T6 | P3 | T5 | O2 | O1 | | | | | | |
| F3 | P4 | F3 | F3 | C3 | C3 | P4 | O2 | FP1 | T4 | | | | | | |
| P3 | C3 | FP1 | C4 | P3 | C4 | C3 | P3 | P3 | C3 | | | | | | |
| C4 | C4 | T6 | T4 | FP2 | O2 | T6 | P4 | F4 | T5 | | | | | | |
| T6 | T5 | T5 | P4 | T5 | P3 | FP2 | C4 | F3 | F4 | | | | | | |
| P4 | F3 | FP2 | C3 | C4 | P4 | T5 | C3 | F7 | P4 | | | | | | |
| F4 | FP2 | P4 | FP2 | F3 | F4 | C4 | FP1 | C4 | C4 | | | | | | |
| FP2 | P3 | T4 | T5 | T4 | T5 | F3 | F3 | C3 | FP2 | | | | | | |
| T4 | F8 | P8 | F4 | F8 | FP1 | F4 | T3 | F8 | F8 | | | | | | |
| F8 | F4 | F4 | P3 | P4 | F8 | T4 | F4 | T3 | F3 | | | | | | |
| F7 | T3 | C4 | F7 | FP1 | T4 | FP1 | T4 | T5 | P3 | | | | | | |
| T5 | F7 | F8 | FP1 | F4 | T3 | F7 | FP2 | P4 | F7 | | | | | | |
| FP1 | T4 | T3 | F8 | F7 | F7 | T3 | F8 | FP2 | T3 | | | | | | |
| T3 | FP1 | F7 | T3 | T3 | FP2 | F8 | F7 | T4 | FP1 | | | | | | |

↑ 60

EEG SIGNAL ANALYSIS SYSTEM

BACKGROUND OF THE INVENTION

1. Field of the Invention

The present invention relates to an electroencephalograph (EEG) signal analysis system which determines, for very small increments of time, frequency values of EEG signals produced at various sites in response to a stimulus or task.

2. Description of the Prior Art

An electroencephalograph (EEG) is a device which measures and records brain wave activity by sensing electrical potential of a patient's scalp, cortex or cerebrum at various sites. Each EEG channel corresponds to a particular electrode combination attached to the patient. The sensed EEG potential at each channel is amplified by a differential amplifier, and the amplifier output signal is typically used to control movement of a recording pen of a polygraph. The EEG record is a long strip of polygraph paper containing a waveform for each EEG channel. The polygraph paper is driven at a predetermined rate (e.g. 30 millimeters per second) and is graduated to represent predetermined time increments. A neurologist must evaluate the EEG record to determine abnormalities in the EEG waveforms.

EEG signals exhibit different frequencies depending upon brain activity. The EEG signal frequencies are classified into four basic frequency bands, which are referred to as "delta" (0 to 3.5 Hertz); "theta" (4 to less than Hertz); "alpha" (8 to 13 Hertz); and "beta" (greater than 13 Hertz). The neurologist determines the predominant frequency of a particular channel during a particular time period by measuring the period of the EEG signal waveform shown on the EEG record. This requires considerable training and is highly dependent upon the skill of the neurologist, since the EEG signal waveform typically includes multiple frequency components.

In general, electronic equipment developed in the past for EEG analysis has been designed primarily for the acquisition of data, with little emphasis on the analysis of that data. Although computers were introduced into EEG technology in the early 1970's, there has been limited acceptance of computer-assisted EEG analysis due to a limited number of channels which are analyzed and a lack of an intuitive display. Existing computerized EEG technology has required a high degree of specialized knowledge to understand the information being displayed and, as a result, the market for that technology has been limited to a relatively small number of specialists in the field of electroencephalography.

One type of EEG signal analysis which has been performed by computers in the past has been called a "spectral analysis". In this type of analysis, the analog EEG signal for each channel is periodically sampled, converted to a digital value and stored. The stored digital data represents an EEG signal waveform (i.e. the amplitude of the EEG signal as a function of time). The computer converts the stored digital data from the time domain to the frequency domain by means of a Fast Fourier Transform (FFT) algorithm. The transformed data represents a frequency spectrum (i.e. amplitude or power of the EEG signal as a function of frequency). The computer provides the frequency spectrum as an output through some form of display.

The analysis of EEG signals in the frequency domain by use of a Fast Fourier Transform has, in the past, placed limits on the shortest time interval over which the EEG signals are sampled. The duration of the time interval determines the period of the lowest frequency in the frequency spectrum produced by the Fast Fourier Transform. Because the EEG signals have very low frequencies, the shortest time interval is typically one second (which corresponds to a lowest frequency of one Hertz). If a shorter time interval were selected, the lowest frequency which could be analyzed would be greater than one Hertz, and thus some or all of the frequencies of interest would be lost. For example, a time interval of twenty milliseconds would result in a lowest frequency of fifty Hertz. The nature of the Fast Fourier Transform and the low frequencies of the EEG signals, therefore, has limited the ability to analyze the frequency content of the EEG signals from various channels during very short time periods of interest.

Despite the development of EEG technology and despite years of study, much remains to be learned as to how the brain processes information. It is theorized that multiple areas of the brain process information in tandem under some type of common control, but the location or origin of that common control is not known. For instance, when a person hears a sound, it reaches the cortex in only about 10 milliseconds. People make decisions on what they have heard at about 60 to 70 milliseconds. These decisions are apparently arrived at after cortical processing, but in the past it has not been possible to determine where the cortical processing is occurring.

In the past, averaging techniques have been used to produce what is known as "Evoked Potentials". In these techniques, an auditory, visual or sensory stimulus is provided, and EEG signals are recorded over a period of time such as 400 to 500 milliseconds. The analog EEG signals are then converted to digital signals, and the digital signals from a series of identical tests are averaged in order to abolish "noise". After successive averaging, a digitized waveform is produced which represents average voltage as a function of time.

Because some of the "noise" which is eliminated by the averaging techniques is the result of cortical activity, the Evoked Potential waveform does not provide an indication of cortical frequency response as a function of time. It is known, however, that the frequency response from a particular portion of the brain does change in reference to use of that portion of the brain.

The frequency response of the cortex cannot be obtained using the Evoked Potential analysis, due to the averaging which is performed to produce the Evoked Potential waveforms. There are, however, cortical components that are seen in the Evoked Potential waveforms. These cortical components are widely distributed, although there is an increased amplitude over the site where they are first received within the cortex. In general, however, the cortical components are difficult to lateralize and hard to localize. The amplitude changes that are seen in the Evoked Potential waveform cannot be well equated with the amount of processing that occurs at that particular site. In fact, it is not even understood whether positivity or negativity of the Evoked Potential waveform means increased or decreased activity. For instance, it is known that if a subject pays attention to a particular sound stimulus, at about 100 milliseconds after that sound stimulus there is an increased negativity of the Evoked Potential waveforms. The significance of this negativity, its cause, or even its location in the cortex is not known.

There is a need for new techniques and equipment for analyzing EEG signals in such a way that a better understanding of the brain's processing of information can be obtained. In particular, there is a need for an EEG signal analyzer which will provide an indication of the frequency response of the cortex (and other structures) and which will demonstrate and record the processing activity of the brain in response to various stimulae or tasks performed.

SUMMARY OF THE INVENTION

The present invention is a signal processing system and method which permits analysis of the frequency of time varying signals (such as EEG signals) over very short epochs (i.e. time periods of interest, which are shorter than the period of the lowest frequency of interest). In the present invention, an analog EEG signal is periodically sampled, converted to digital data, and stored.

For each epoch, at least one digitized waveform is produced which has a length at least equal to the period of the lowest frequency of interest and which includes digital data corresponding to the epoch. The digitized waveform is transformed from the time domain to the frequency domain to create a frequency spectrum which has a frequency content uniquely attributable to the digital data corresponding to the epoch. A frequency value for the epoch (such as a weighted mean frequency value) is derived from the frequency spectrum corresponding to that epoch.

By using frequency spectra corresponding to different staggered time intervals, frequency values representing frequency response during other epochs are obtained. This allows analysis of changes in frequency response with time.

The present invention, therefore, permits measurement of the frequency response from a selected site during epochs which are much shorter than the period of the lowest frequency of interest. This overcomes the shortcomings of previous EEG signal analysis techniques in which the shortest possible epoch is equal to the period of the lowest frequency of interest.

BRIEF DESCRIPTION OF THE DRAWINGS

FIG. 1 is an electrical block diagram of a preferred embodiment of the EEG signal analyzer of the present invention.

FIG. 2 is a diagram illustrating typical electrode sites used in a sixteen channel EEG electrode array.

FIG. 3 is a graph illustrating staggered time intervals used in an embodiment of the present invention referred to as Interval Overlap Processing.

FIG. 4 is a block diagram of a portion of the EEG signal analyzer of FIG. 1 as used in an embodiment referred to as Interval Subtraction Processing.

FIGS. 5A and 5B are graphs illustrating two different embodiments of the staggered time intervals which define selected epochs in Interval Subtraction Processing.

FIGS. 6, 7, 8 and 9 illustrate three different forms of displayed or printed output provided by the system of FIG. 1 to illustrate changes in frequency response for each EEG channel during a succession of epochs.

DETAILED DESCRIPTION OF THE PREFERRED EMBODIMENTS

General Description

Figure 6:
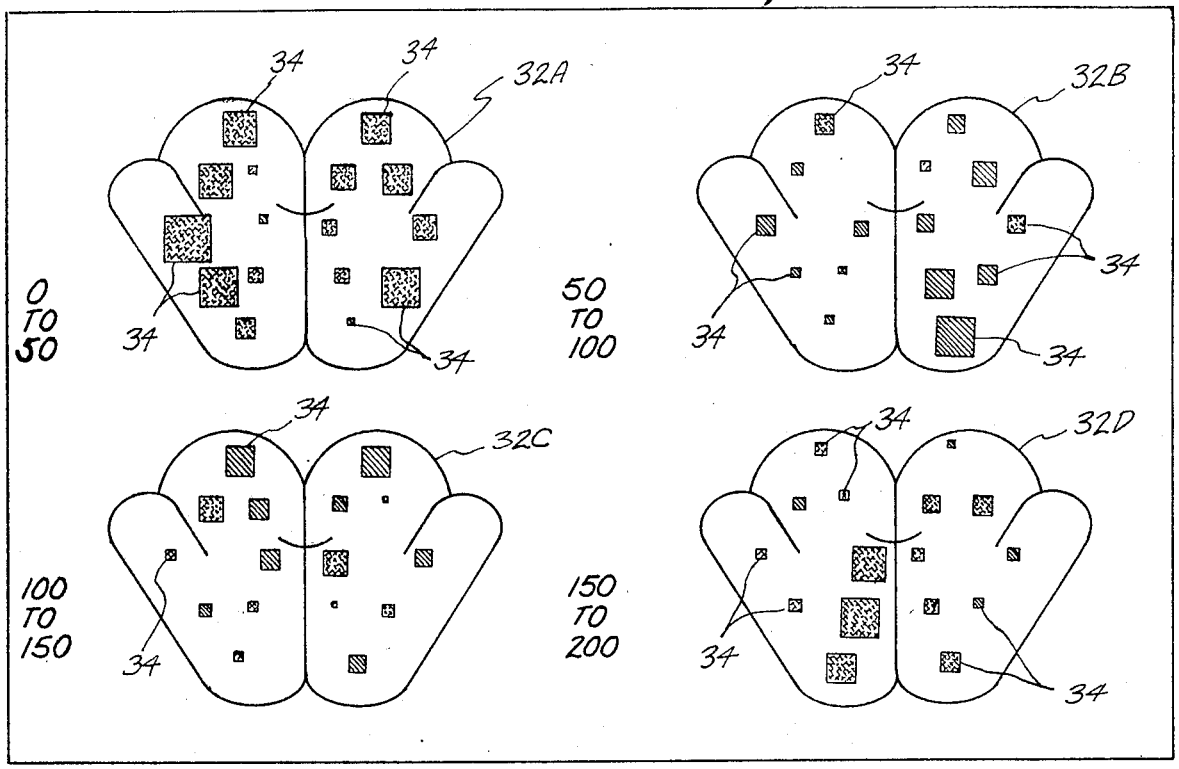

FIG. 1 shows a preferred embodiment of EEG signal analyzer 10 of the present invention. In this embodiment, EEG signal analyzer 10 includes EEG electrode array 12, EEG multichannel amplifier circuit 14, signal processing module 16, digital computer 18, computer disc storage 19, stimulus source 20, display 22, printer or other hard copy device 24, and keyboard 26. The purpose of EEG signal analyzer 10 is to record and analyze EEG signals produced in response to a stimulus from stimulus source 20 (or in response to a task performed by a human subject) and to provide an output through display 22 or printer 24 which indicates the frequency response of EEG signals from various sites during a series of very short epochs. The epochs are of sufficiently short duration (preferably 50 milliseconds or less) so that the changes in EEG frequency response at various sites with time during the time period when cortical processing occurs can be studied.

EEG electrode array 12 includes a plurality of EEG electrodes which are placed in contact with the scalp of a human subject. FIG. 2 is a diagram which illustrates nineteen typical sites of electrodes on a subject's head 28. When array 12 is used in a sixteen channel system, sixteen of the nineteen sites shown in FIG. 2 are used. In the diagram shown in FIG. 2, the electrode sites are identified by the commonly used designations Fp1, Fp2, F0, F3, F4, F7, F8, T3, T4, T5, T6, C0, C3, C4, P0, P3, P4, 01, and 02. Also shown are reference electrode sites (A1 and A2) for reference electrodes which are commonly attached to one (or both) of the subject's ears.

Each EEG channel represents one of the EEG electrode sites of array 12. EEG multichannel amplifier circuit 14 includes a differential amplifier for each channel, which amplifies the potential difference between a reference potential and the potential at the electrode site for that particular channel. The reference potential is typically derived from one or a combination of both of the reference electrode sites A1 or A2, or is based upon an average of the potentials from all of the sites. The output of EEG multichannel amplifier circuit 14 is an analog EEG signal for each channel.

Signal processing module 16 receives the analog EEG signals from EEG multichannel amplifier circuit 14. Signal processing module 16 samples the analog EEG signal for each channel at a rate which is greater than twice the highest frequency of interest. The sampled analog values for each channel are converted to digital values, and are stored by signal processing module 16. During each test, the sampling, digitizing and storing occurs over a time interval which is at least as long as the period of the lowest EEG signal frequency of interest, and which is initiated at a predetermined time either before or after a stimulus. In a preferred embodiment, the lowest frequency of interest is one Hertz, and therefore the time interval has a duration of at least one second. The stored digital sample values for each channel represent the amplitude of the EEG signal as a function of time.

During each test, stimulus source 20 preferably provides a visual, auditory or other sensory stimulus to the human subject, and signal processing module 16 samples, digitizes and stores the EEG signals from the various channels. At the end of each test, the stored digital sample values are transferred from signal processing module 16 to digital computer 18 and is stored in computer disc storage 19 or in random access memory (RAM) within computer 18. The test is typically repeated a number of times (N) using identical time intervals.

Digital computer 18 determines a weighted mean frequency value (WMF) for each epoch (i.e. a time period of interest) at each channel based upon the digital sample values received from signal processing module 16. Based upon the weighted mean frequency (WMF) values for the various epochs and channels, digital computer 18 provides an output through display 22 or printer 24 which indicates the frequency response of the EEG signals from the various channels during a series of epochs. In this way, the frequency response at various cites as a result of the stimulus can be observed and studied.

In the following description, four different embodiments of the present invention will be described in detail. These embodiments will be referred to as "Interval Overlap Processing", "Interval Subtraction Processing", "Zero Fill Processing", and "Interval Subtraction with Zero Fill Processing".

In general, each of these embodiments involves the transformation of digitized waveforms from the time domain to the frequency domain. Each digitized waveform which is transformed has a length which is at least as long as the period of the lowest frequency of interest and includes digital sample values which are unique to a particular epoch. The transformation results in a frequency spectrum which has a frequency content which is unique to that particular epoch.

In one preferred embodiment, the transformation from the time domain to the frequency domain is performed by digital computer 18 using a signal processing algorithm such as a Fat Fourier Transform. In other embodiments of the present invention, however, the transformation is performed by signal processing hardware within signal processing module 16. In either case, the result is a frequency spectrum for each channel based upon a digitized waveform which is at least as long as the period of the lowest frequency of interest and which includes a digital sample value unique to the particular epoch.

A weighted mean frequency (WMF) value for each epoch at each channel is then calculated by a digital computer 18 based upon the corresponding frequency spectrum. As a result, each of the WMF values for a particular channel represents a particular epoch, because it is the frequency content of that particular epoch which makes that WMF value different from other WMF values for that same channel.

Using the stored WMF values, digital computer 18 calculates a RANGE of WMF values for each channel. The RANGE represents the difference between the highest and lowest WMF values for that channel.

Digital computer 18 then calculates a weighted mean frequency difference (WMFD) value for each epoch at each channel. In one preferred embodiment of the present invention, WMFD=WMF=WMFA, where WMFA is the average of the WMF values at that channel over all of the various epochs.

In another preferred embodiment, WMFD=WMF−WMFB, where WMFB is a base line value which is a WMF value from a time interval which both begins and ends prior to the stimulus. In other words, the WMFB value represents the weighted mean frequency at that particular channel when the human subject is unaffected by the stimulus.

Digital computer 18 then calculates, for each epoch at each channel, an adjusted frequency value (AFV). In a preferred embodiment of the present invention, AFV=WMFD/RANGE.

Based upon the WMF values, the WMFD values, and the AFV values, digital computer 18 produces one of a number of different outputs through display 22 or printer 24. As will be described in further detail later in this specification, the outputs preferably illustrates frequency response of the EEG signals of various channels by showing AFV as a function of epoch, WMF as a function of epoch and a ranking of the various channels as a function of their WMF and AFV value for each of the epochs.

INTERVAL OVERLAP PROCESSING

In the preferred embodiment of the present invention which is termed "Interval Overlap Processing", the sampling, digitizing and storing of the EEG signal is performed during a series of different time intervals which are slightly staggered in time with respect to the stimulus. FIG. 3 shows an example of the different time intervals which are used during the Interval Overlap Processing of the present invention. In FIG. 3, the time when the stimulus is triggered is designated as T=0, and the epochs are shown as having a 50 millisecond duration.

In FIG. 3, four different overlapping time intervals labeled Interval A, Interval B, Interval C and Interval D are shown. Each interval has a duration of one second. Interval A begins at T=−950 ms and ends at T=50 ms. Interval B begins at T=−900 ms and ends at T=100 ms. Interval C begins at T=−850 ms and ends at T=150 ms. Interval D begins at T=−800 ms and ends at T=200 ms.

Digital computer 18 coordinates the operation of signal processing module 16 and stimulus source 20 so that the beginning of the interval has a predetermined time relationship to the stimulus. Depending upon the particular epoch of interest, the interval may begin before or after the stimulus. The time period T between the beginning of the interval and the occurrence of the stimulus is:

$$T = X\, T_E \qquad \text{Eq. 1}$$

where $0 < X < 1 +$ (integer value of $T_I/T_E$)

$T_E$ = time duration of epoch $T_I$ = time duration of interval

As can be seen from FIG. 3, Intervals A, B, C and D are of equal length, but are staggered slightly at both ends. When a weighted mean frequency value for Interval A is compared with the weighted mean frequency value from Interval B, any differences in those two weighted mean frequency values are attributable to two relatively short time periods. The first is designated as "Tail #2" and represents the time period during which only Interval A (but not Interval B) occurs. The other time period is labeled "Epoch #2" (because it is the second 50 ms epoch after the stimulus), and represents the time period during which Interval B (but not Interval A) occurs.

Similarly, any difference in weighted mean frequency values for Interval B and Interval C is due to the portion labeled "Tail #3" and the portion labeled "Epoch "#3" in FIG. 3. Any difference between weighted mean frequency values of Interval C and Interval D is due to Tail #4 and Epoch #4.

The contribution to any change in the weighted mean frequency value from one interval to another is due primarily to the epochs following shortly after the stimulus, as opposed to the tails which precede the stimulus. This is because the frequency response prior to the stimulus is relatively unchanged, and any significant change in frequency is primarily due to changes in processing activity subsequent to the stimulus.

In Interval Overlap Processing, a total of N tests are performed for each of the intervals. This permits averaging of the weighted mean frequency values for each of the intervals, so as to reduce the effect of noise on the determination of a WMF value for each epoch at each channel.

At the end of each test, the digitized waveforms for each of the channels are transferred from signal processing module 16 to digital computer 18. Table 1 outlines the steps which are performed by digital computer 18 in converting the digital sample values to weighted mean frequency (WMF) values, weighted mean frequency difference (WMFD) values, and adjusted frequency values (AFV). From these values, digital computer 18 produces the outputs which are supplied through display 22 and printer 24.

TABLE 1

1.1 The digital sample values for each channel and time interval are used to form a digitized waveform of a length equal to or greater than the period of the lowest EEG signal frequency of interest. Each digitized waveform is multiplied by a window function. In one preferred embodiment, the window function is a four term Blackman-Harris window function, although other window functions may also be used in accordance with the present invention.

1.2 Each digitized waveform (modified by the window function) is transformed from the time domain to the frequency domain to produce a frequency spectrum for the corresponding channel during that particular time interval.

1.3 A weighted mean frequency WMF is calculated from the frequency spectrum for each channel for the particular interval.

$$WMF = \Sigma \frac{(Hz)(Amplitude)}{Total\ Amplitude} \qquad Eq.\ 2$$

1.4 The WMF values are stored in RAM storage within digital computer 18 and/or in computer disc storage 19.

1.5 The WMF value for each channel is averaged with other WMF values for that channel from preceding tests based upon the same time interval.

1.6 Steps 1.1 through 1.5 are repeated N times for each time interval until all intervals have been completed.

1.7 For each channel, the range of WMF values for the various intervals is calculated.

$$RANGE = WMF_{Highest} - WMF_{Lowest} \qquad Eq.\ 3$$

1.8 The average weighted mean frequency WMFA is calculated for each channel.

1.9 The weighted mean frequency difference WMFD is calculated for each epoch at each channel.

$$WMFD = WMF - WMFA \qquad Eq.\ 4A$$

or $$WMFD = WMF - WMFB \qquad Eq.\ 4B$$

1.10 For each epoch, at each channel an adjusted frequency value (AFV) is calculated.

$$AFV = WMFD/RANGE \qquad Eq.\ 5$$

1.11 Based upon the particular display or print function selected by the user through keyboard 26, digital computer 18 displays information based upon the WMF values, the WMFD values, and the AFV values for the various channels and epochs.

INTERNAL SUBTRACTION PROCESSING

Although Interval Overlap Processing provides frequency response information for epochs which are much shorter than the period of the lowest frequency of interest, a large amount of the frequency response data is based upon portions of the digitized waveform which are not of interest. This tends to minimize the effects caused by changes in frequency response from one epoch to the next. Internal Subtraction Processing provides a more accurate determination of frequency response during the various epochs by cancelling out the effects of those portions of two staggered intervals which overlap. As a result, the weighted mean frequency values which are derived using Interval Subtraction Processing are due solely to the epoch and tail portions produced by two slightly staggered intervals (Interval A' and Interval B').

In the Interval Subtraction Processing embodiment of the present invention, signal processing module 16 includes a pair of identical signal processing modules 16A and 16B shown in FIG. 4 which operate in parallel during each test to sample, digitize and store digital values during slightly staggered time intervals A' and B'. The digitized waveform corresponding to Interval A' is stored by signal processing module 16A, while the digitized waveform corresponding to Interval B' is stored by signal processing module 16B.

FIGS. 5A and 5B show two different embodiments of the Interval Subtraction Processing of the present invention, in which Intervals A' and B' are used to define epochs which are much shorter duration than the period of the lowest EEG signal frequency of interest. In the examples shown in FIGS. 5A and 5B, the epochs have a 50 millisecond duration. The particular epoch which is defined in both FIG. 5A and FIG. 5B is designated "Epoch #2", because it is the second 50 millisecond epoch subsequent to the stimulus. Epoch #2 begins 50 milliseconds after the stimulus has been provided, and ends 100 milliseconds after the stimulus has been provided. In both examples, the time when the stimulus is triggered is designated T=0, the beginning of Epoch #2 is designated T=50 ms, and the end of Epoch #2 is designated T=100 ms.

In the embodiment shown in FIG. 5A, Interval A' and Interval B' are each of one second duration. Interval A' begins at T=50 ms and ends at T=1050 ms, while Interval B' begins at T=100 ms and ends at T=1100 ms.

As shown in FIG. 5A, Epoch #2 is defined by the time period when Interval A' is present and Interval B' has not yet started. There is also a portion which is designated "Tail #2" which is a period from T=1050 ms to T=1100 ms when Interval B' is still present, but Interval A' has ended. Other than the portion designated "Epoch #2" and the portion designated "Tail #2", Interval A' and Interval B' are identical. In other words, the EEG signals which are sampled, digitized and stored from T=100 ms to T=1050 ms will be identical for signal processing modules 16A and 16B, since both Interval A' and Interval B' are present.

In the embodiment of FIG. 5A, digital computer 18 coordinates the operation of signal processing modules 16A and 16B and stimulus source 20 to produce the desired time relationship between Intervals A' and B'. In a preferred embodiment of the present invention, digital computer 18 loads signal processing module A with a first digital value which represents the desired time delay before commencement of Interval A' ("Delay A" shown in FIG. 5A) and loads signal processing module 16B with a second digital value corresponding to the desired time delay before commencement of Interval B' ("Delay B" shown in FIG. 5A). Signal processing module 16A receives a trigger signal from digital computer 18 when the stimulus is triggered and begins timing Delay A. When Delay A has been completed, signal processing module 16A begins Interval A', during which it samples, digitizes and stores the EEG signals for each channel.

Similarly, signal processing module 16B receives the trigger signal from digital computer 18 when the stimulus is triggered, and begins timing Delay B. When Delay B is completed, signal processing module 16B begins Interval B' during which it samples, digitizes and stores the EEG signals for each channel.

FIG. 5B shows another embodiment which is used to produce Intervals A' and B'. In this embodiment, Intervals A' and B' are commenced prior to the stimulus, rather than after the stimulus as in FIG. 5A. In the particular example shown in FIG. 5B, Interval B+ is commenced first (at T=−950 ms), and Interval A' is started 50 milliseconds later (at T=−900 ms). 950 milliseconds after Interval B' has started (i.e. at T=0), digital computer 18 triggers stimulus source 20 to produce the stimulus. Interval B' continues for a one second duration, and ends at T=50 ms. Interval A' is also a one second duration, and ends at T=100 ms.

In the embodiment shown in FIG. 5B, Epoch #2 is again of 50 millisecond duration, and starts at T=50 ms and ends at T=100 ms. Epoch #2 is defined as the time period when only Interval A' is present.

In the embodiment shown in FIG. 5B Tail #2 begins at T=−950 ms and ends at T=−900 ms. Tail #2 in this case occurs prior to the stimulus, and is defined as the time period when only Interval B' is present.

When the embodiment shown in FIG. 5B is used, digital computer 18 again coordinates the operation of signal processing modules 16A and 16B and stimulus source 20. In that case, digital computer 18 determines for the desired epoch (1) the time delay between the commencement of Interval B' and the commencement of Interval A' and (2) the time delay from the commencement of Interval B' until the stimulus provided by stimulus source 20 is triggered.

In either of the embodiments shown in FIG. 5A or 5B, the test for a particular epoch is repeated N times. For each epoch, digital computer 18 determines the appropriate commencement times for Intervals A and B and initiates a series of N tests. At the end of each test, the digital sample values for each channel are transferred from signal processing module 16A to digital computer 18 and from signal processing module 16B to digital computer 18.

The digital signal processing performed by digital computer 18 in the Interval Subtraction Processing embodiment of the present invention is generally similar to that described previously with respect to the Interval Overlap Processing embodiment, with one important difference. In the Interval Subtraction Processing embodiment, digital computer 18 transforms the digitized waveforms formed by the digital sample values from the two signal processing modules 16A and 16B separately to produce frequency spectrum A and B frequency spectrum for each channel and then subtracts frequency spectrum B from frequency spectrum A to produce a frequency spectrum D. The resulting frequency spectrum D represents a difference frequency spectrum which corresponds only to the epoch and tail portions defined by Interval A and Interval B. Those portions of frequency spectrum A and frequency spectrum B which are based upon the overlapping portions of Intervals A and B cancel one another.

Table 2 outlines the steps performed by digital computer 18 in the Interval Subtraction Processing of the present invention.

TABLE 2

2.1 The digital sample values from Intervals A and B are used to form a part of digitized waveforms for each channel. The pair of digitized waveforms are slightly staggered in time, are of equal length and have a length equal to or greater than the period of the lowest signal frequency of interest. These two digital waveforms for each channel are multiplied by the window function.

2.2 The pair of digitized waveforms (modified by the window function) for each channel are transformed independently from the time domain to the frequency domain. This independently yields a frequency spectrum A and a frequency spectrum B for each channel.

2.3 For each channel, frequency spectrum B is subtracted from frequency spectrum A to yield a difference frequency spectrum D for each channel. Frequency spectrum D for each channel is used in the subsequent calculations of weighted mean frequency.

2.4 Steps 1.3 through 1.11 of Table 1 are performed.

From the foregoing description, it can be seen that the values of WMF, WMFD, and AFV produced by Interval Subtraction Processing do not contain the overlapping portions of Intervals A' and B', but do include frequency response not only from the epoch, but also from the corresponding tail. The inclusion of the portion of the data which corresponds to the tail, however, does not significantly detract from the accuracy of the WMF, WMFD and AFV values for several reasons.

First, the tail occurs a substantial period after (in FIG. 5A) or before (in FIG. 5B) the stimulus is triggered. The EEG frequency response associated with the "tail", therefore, is not significantly affected by the stimulus and is in effect a "base line" or constant factor in all of the measurements. On the other hand, the EEG frequency response associated with the epoch varies significantly with time from the stimulus as well as from site to site. The WMF, WMFD and AFV values can, therefore, be attributed to the data from the epoch rather than the tail portions.

Second, the averaging of the WMF values for each epoch at each channel over a plurality of tests tends to reduce the significance of any effect of the data from the tail. Since the frequency response during the tail is not affected to any significant degree by the stimulus, it is more likely to be random than is the frequency response from the epoch. Averaging the WMF values causes random changes in frequency response from test to test to be minimized in comparison to the consistent changes in frequency response caused by the stimulus.

ZERO FILL PROCESSING

The Zero Processing embodiment of the present invention provides higher accuracy than Interval Overlap Processing, without requiring multiple signal processing modules operating in parallel, as in Interval Subtraction Processing. In Zero Fill Processing, a total of N tests are performed using a time interval which is sufficiently long so that it includes all of the epochs which are to be analyzed. Digital computer 18 coordinates the operation of signal processing module 16 and stimulus source 20, so that the interval is triggered a predetermined period of time prior to or after the stimulus. At the end of each test, the digital sample values for each channel are transferred to digital computer 18 by signal processing module 16. The steps which are then performed by digital computer 18 are described in Table 3.

TABLE 3

3.1 The digital sample values corresponding to a selected epoch and channel are selected and are placed in the center of a digitized waveform with equal numbers of "0's" on opposite sides. The digitized waveform has a length equal to or greater than the period of the lowest EEG signal frequency of interest. For example, if the sample rate is 128 samples per second and the epoch is from T=50 ms to T=100 ms, the six sample points corresponding to that epoch used to create a modified digitized waveform of 128 sample points (i.e. a length of one second, corresponding to a lowest frequency of one Hertz). In this digitized waveform, the first 61 sample points (Nos. 1 through 61) and the last 61 samples (Nos. 68 through 128) are "0", while the six sample values corresponding to the epoch are points Nos. 62 through 67.

3.3 The nonzero points of the digitized waveform are multiplied by the window function.

3.4 The digitized waveform (as modified by the window function) for each channel is transformed from the time domain to the frequency domain to produce a frequency spectrum for that epoch and channel.

3.5 Steps 3.1 through 3.4 are repeated for each epoch and channel until a frequency spectrum for each epoch at each channel has been produced.

3.6 Steps 1.3 through 1.11 of Table 1 are performed.

INTERVAL SUBTRACTION WITH ZERO FILL PROCESSING

Still further accuracy in the determination of frequency response is obtained using a combination of Interval Subtraction Processing and Zero Fill Processing described previously. In this embodiment, which is referred to as Interval Subtraction With Zero Fill Processing, only a single signal processing module 16 is required. A total of N tests are performed over a time interval which is sufficiently long so that all epochs of interest are included within the interval. Digital computer 18 coordinates the operation of the signal processing module 16 and the stimulus source 20 so that the time interval is triggered a predetermined period of time prior to or after the stimulus.

At the end of each test, the digital sample values from each channel are transferred from signal processing module to digital computer 18. Table 4 describes the steps performed by digital computer 18 upon receiving the digital sample values.

TABLE 4

4.1 The digital sample values corresponding to a first predetermined portion of the time interval are placed in the center of a first digitized waveform and are equally bounded on each side by "0's". The first predetermined portion either begins or ends with one of the boundaries of the selected epoch. The length of the first digitized waveform is equal to or greater than the period of the lowest frequency of interest.

4.2 The non-zero digitized points in the first digitized waveform are multiplied by the window function.

4.3 The first digitized waveform (as modified by the window function) is transformed from the time domain to the frequency domain to produce a frequency spectrum A.

4.4 The digital sample values corresponding to a second predetermined portion of the time interval are placed within a second digitized waveform, equally bounded by "0's". The second predetermined portion is of equal length but is shifted in time with respect to the first portion, and either begins or ends with the other boundary of the epoch. Only one of the first and second portions, therefore, includes digital sample values from the epoch. The second digitized waveform is of equal length to the first digitized waveform.

4.5 The nonzero digitized points of the second digitized waveform are multiplied by the window function.

4.6 The second digitized waveform (as modified by the window function) is transformed from the time domain to the frequency domain to produce a frequency spectrum B.

4.7 Frequency spectrum B is subtracted from frequency spectrum A to produce a difference frequency spectrum D.

4.8 Steps 4.1 through 4.7 are repeated until a frequency spectrum D for each epoch at each channel is produced.

4.9 Steps 1.3 through 1.11 of Table 1 are performed.

OUTPUT FUNCTIONS

Digital computer 18 provides outputs through display 22 and printer 24 based upon the stored values of WMF, WMFD and AFV. The particular output selected is based upon information provided to digital computer 18 through keyboard 26 or some other user input interface (such as a light pen input device used with display 22).

FIGS. 6, 7, 8 and 9 show examples of different visual outputs which preferably are provvidded by the present invention through display 22, printer 24, or both. The particular visual output and the output device (display 22 or printer 24) are user-selectable through keyboard 26.

Visual output 30 shown in FIG. 6 consists of four head graphics 32A–32D which are generally similar to the diagram shown in FIG. 2. Each head graphic 32A–32D represents one of the epochs in the series. Head graphic 32A is for Epoch #1, head graphic 32B represents Epoch #2, and so on. When more than four epochs are of interest, visual output 30 comprises multiple "screens", each of which includes a set of four different epochs. The particular "screen" of visual output 30 is user selectable through keyboard 26.

In FIG. 6, each head graphic 32A–32D includes squares 34 of variable size and color. The location of squares 34 correspond to the electrode sites of electrode array 12 which are being used. In one embodiment of the present invention, the particular electrode site being used can vary, and digital computer 18 is supplied with an indication of the sites in use and the channel which correspond to those sites by the user through keyboard 26.

The color of each square 34 based on the sign of AFV and indicates whether WMF at that particular site during that particular epoch is greater or less than either an average or a base line weighted mean frequency value (WMFA or WMFB). If the stored value of AFV is negative, the square is colored red. Conversely, if AFV is positive, the square is colored green.

The size of each square 34 is a function of the magnitude of the AFV. The larger the magnitude, and the larger the area of square 34.

Visual output 30 shown in FIG. 6, therefore, provides a visual representation of the frequency response at the various electrode sites from epoch-to-epoch. This permits an easy and intuitive comparison of the brain processing activity in response to a stimulus at various sites as a function of time.

Figure 7:
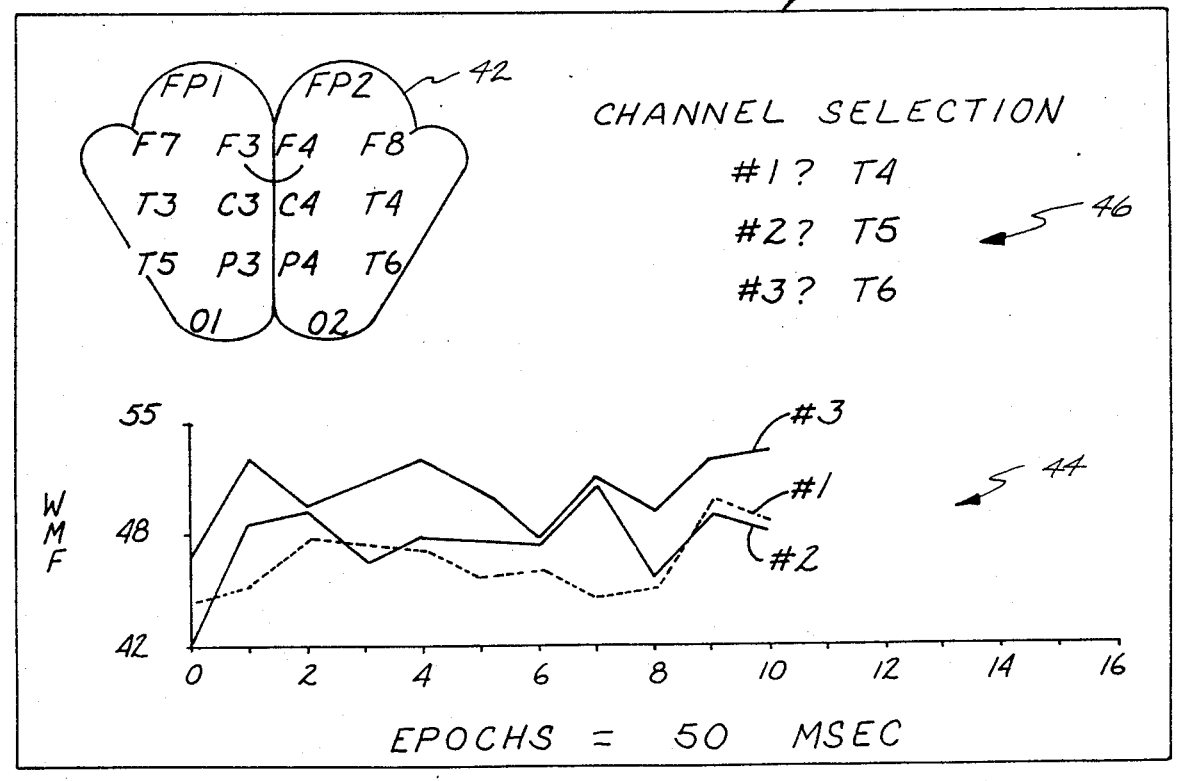

Visual output 40 shown in FIG. 7 includes a head graphic 42 showing the designations for each site, a graph 44 showing weighted mean frequency WMF as a function of time for three selected sites and an information field 46 showing which curve (#1, #2, #3) corresponds to which site. The curves plotted in FIG. 7 are based upon the stored WMF values for the selected sites (or channels) during the the various epochs.

FIG. 8 shows visual output 50, which is based upon the AFV data stored by digital computer 18. Visual output 50 shown in FIG. 8 is in the form of a chart which is displayed by display 22 or printed by printer 24. In generating visual output 50, digital computer 18 sorts the values of AFV for the various sites by magnitude and sign for each epoch. In the particular example shown in FIG. 8, the site exhibiting the largest positive AFV is ranged at the top and the other sites are arranged vertically in descending order, with the site having the largest negative AFV at the bottom of each vertical column. There is a vertical column for each epoch.

FIG. 9 shows visual output 60, which is a chart similar to visual output 50, except that it is based upon WMF values rather than AFV values. In preferred embodiments, the user can designate a particular site (through keyboard 26), and visual output 50 or 60 will include shaded or colored boxes 62 to highlight the position of that site in the chart. This feature is illustrated in FIG. 9 with site 01.

It can be seen, of course, that other forms of output based upon the stored WMF, WMFD and AFV values are possible, depending upon the needs and desires of the medical and scientific personnel using system 10. An important advantage of the present invention is that the WMF and digital sample data is stored in computer disc storage 19 so that it can be used later to create other forms of output which are desired.

SIGNAL PROCESSING MODULE 16

Figure 10:
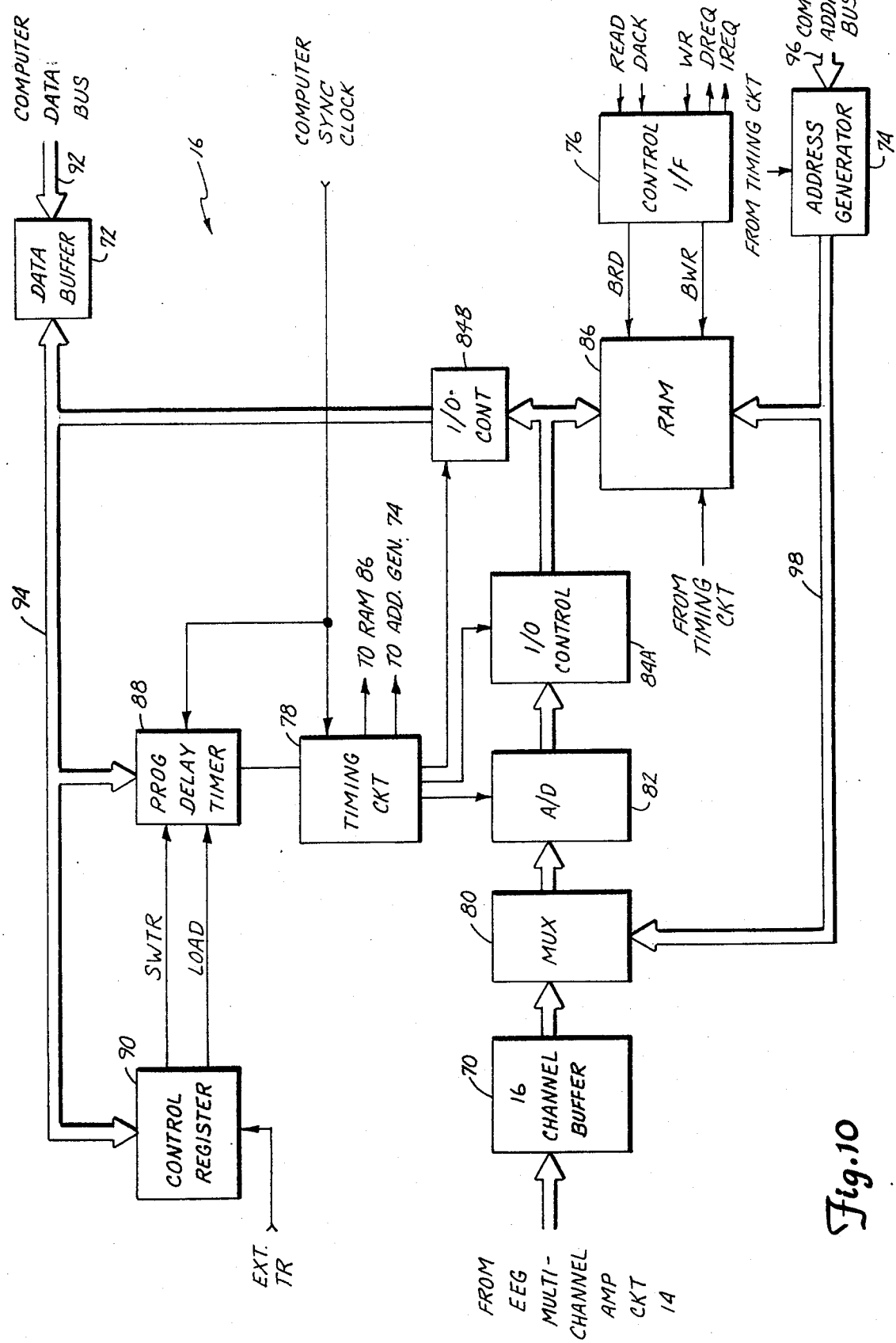
FIG. 10 is an electrical block diagram of the preferred embodiment of the signal processing module of the EEG signal analyzer of FIG. 1.

In one preferred embodiment of the present invention, digital computer 18 is an IBM personal computer which has had its read/write random access memory (RAM) capacity increased to at least 96K bytes of data. FIG. 10 shows a preferred embodiment of signal processing module 16 which is used in conjunction with the IBM personal computer in this preferred embodiment. When two signal processing modules 16A and 16B are used (as in the Interval Subtraction Processing embodiment), each module 16A and 16B is preferably of the form shown in FIG. 10. The particular preferred embodiment shown in FIG. 10 is for a sixteen channel EEG system.

Signal processing module 16 shown in FIG. 10 includes sixteen channel buffer 70, data buffer 72, address generator 74, control interface 76, timing circuit 78, multiplexer (MUX) 80, analog-to-digital converter (A/D) 82, input/output (I/O) control 84A and 84B, random access memory (RAM) 86, programmable delay timer 88, and control register 90. It should be noted that programmable delay timer 88 is necessary for only the Interval Substraction embodiment.

Signal processing module 16 interfaces with EEG multichannel amplifier circuit 14 through sixteen channel buffer 70. Signal processing module 16 interfaces with digital computer 18 through data buffer 72, address generator 74, control interface 76, and timing circuit 78. Data buffer 72 acts as a buffer between data bus 92 of computer 18 and module data bus 94. Digital data flowing between signal processing module 16 and digital computer 18 passes through data buffer 72.

Address generator 74 receives addresses from computer address bus 96 during computer read operations and generates its own addresses during sampling operations, and provides those addresses to multiplexer 80 and RAM 86 on module address bus 98. Control interface 76 is connected to the READ, DACK, IREQ, WR and DREQ lines of digital computer 18. Control interface 76 provides a read signal (BRD) and a write signal (BWR) to RAM 86 based upon the control signals from digital computer 18.

Timing circuit 78 and programmable delay timer 88 each receive a synchronized clock from digital computer 18. The timing signals produced by timing circuit 78 based upon this synchronized clock signal from computer 18 are supplied to A/D converter 82, I/O controls 84A and 84B, RAM 86, and address generator 74.

In the embodiment shown in FIG. 10, digital computer 18 controls the relative timing of the commencement of the interval with respect to the triggering of the stimulus through programmable delay timer 88 and control register 90. Digital computer 18 supplies a digital value on data bus 92 which is supplied through data buffer 72 onto module data bus 94. This digital word causes control register 90 to supply a LOAD signal to programmable delay timer 88, which loads selected bits of that digital word which represent the desired duration of a delay. When digital computer 18 initiates a test, a digital word is provided through data bus 92, data buffer 94, and system data bus 96 to control register 90, which supplies a trigger signal SWTR to programmable delay timer 88. This causes programmable delay timer 88 (which is preferably a count down counter) to begin counting in response to the synchronized clock signal. When programmable delay timer 88 times out, it provides a signal to timing circuit 78, which indicates the end of the delay, and the beginning of the time interval. Digital computer 18 triggers stimulus source 20 either at the same time it initiates the test or at a predetermined time period thereafter.

In the embodiment shown in FIG. 10, programmable delay timer 88 can also be triggered as a result of an external trigger signal (EXT TR) which enables control register 90 to produce the SWTR signal. The external trigger signal is used in those embodiments in which stimulus source 20 is triggered independently of digital computer 18. This permits signal processing module 16 to coordinate its operation with stimulus source 20 in those embodiments.

When timing circuit 78 has been enabled by the signal from programmable delay timer 88, it begins producing timing signals, and continues to produce those timing signals until the interval is completed. During the interval, the analog EEG signals received from multichannel amplifier circuit 14 are buffered by sixteen channel buffer 70 and supplied to multiplexer 80. The analog EEG signal from one channel at a time is supplied by multiplexer 80 to A/D converter 82 to be sampled and digitized. The particular channel which is selected is based on an address from address generator 74, which changes addresses at a rate determined by a timing signal from timing circuit 78. In a preferred embodiment of the present invention, a different channel is selected by multiplexer 80 each 245 microseconds. During one second, the analog EEG signal for each of the sixteen channels is sampled and digitized 256 times. It will be understood, however, that other sample rates can also be advantageously used in the present invention.

The digital sample values produced by A/D converter 82 are supplied through I/O control 84 to RAM 86. Each sample value is stored in a different location of RAM 86, which depends upon the address supplied by address generator 74 and the time at which the signal was sampled. When the interval is completed, there are digital sample values stored in RAM 86 for each of the sixteen channels. These digital sample values represent the amplitude of the analog EEG signal for that particular channel as a function of time.

Timing circuit 78 supplies a timing signal to I/O control 80 which permits the stored data from RAM 86 to be read out of RAM 86 through I/O control 80, module data bus 94, and data buffer 72 onto computer data bus 92. It is this stored data which is then processed in the manner previously described.

In another embodiment of the present invention, RAM 86 is divided into two separate memory banks in a double buffered arrangement. The digital sample values from A/D converter 82 are written into the first memory bank during the first half of the interval, and into the second memory bank during the second half of the interval. The digital sample values which have been written into the first memory bank are read out during the second half of the interval. Similarly, the digital sample values from the second memory bank are read out after the test or during the first half of the interval of the next test. This arrangement reduces the time required to transfer the data from signal processing module 16 to digital computer 18.

CONCLUSION

The present invention, by determining weighted mean frequencies at various sites during very short epochs, permits medical and scientific personnel to study and reconstruct the brain's processing of information. As a result, the present invention has a wide range of applications.

First, the present invention provides a new method and system for viewing nervous system functions.

Second, the present invention has applicability as a clinical aid in the documentation of cerebral dysfunction.

Third, the present invention provides a new and powerful research tool for use in unravelling the processing of nervous activity.

Fourth, the present invention provides a quantitative method of assessing the effects of drugs on the central nervous system.

Fifth, the present invention provides a means for quantitative rather than just qualitative measures of residual functional capacity. An example of this type of application of the present invention is in the determination of temporary or permanent disability of a patient after a stroke or other physical trauma.

Sixth, the system of the present invention also provides a means by which assessment of psychiatric patients may be possible.

Seventh, although the present invention is particularly useful in processing EEG signals, it has applicability to the processing of other time-varying biological signals (such as electrocardiograph (EKG) signals or other neurological signals) as well.

Although the present invention has been described with reference to preferred embodiments, workers skilled in the art will recognize that changes may be made in form and detail without departing from the spirit and scope of the invention.

What is claimed is:

1. A method of processing an EEG signal to provide an indication of cerebral activity in response to an event, the method comprising:
   sampling the EEG signal to produce digital sample values representative of amplitude of the EEG signal as a function of time;
   providing a plurality of digitized waveforms which are based at least in part on the digital sample values, which have a first length, and each of which includes fill values surrounding the digital sample values derived from one of a plurality of epochs having different time relationships to the event, each epoch having a second length which is less than the first length;
   transforming each digitized waveform from a time domain to a frequency domain to produce a frequency spectrum corresponding to one of the plurality of epochs, each frequency spectrum having frequency components uniquely attributable to the digital sample values derived from its corresponding epoch;
   deriving a frequency value for each epoch based upon the frequency spectrum corresponding to that epoch; and
   providing an output indicative of cerebral activity based upon the frequency values.

2. The method of claim 1 wherein providing an output indicative of cerebral activity comprises:
   comparing the frequency value for each epoch with a reference frequency value to produce a frequency difference value for each epoch; and
   providing the output as a function of the frequency difference values.

3. The method of claim 2 wherein the reference frequency value is a calculated frequency value from a frequency spectrum based upon a digitized waveform which began and ended prior to the event.

4. The method of claim 2 wherein the reference frequency value is an average mean frequency, and wherein the method comprises:
   averaging the frequency values for the plurality of epochs to produce the reference frequency value.

5. The method of claim 2 wherein providing the output as a function of the frequency difference values comprise:
   comparing a maximum and a minimum calculated frequency value from among the frequency values for the plurality of epochs to produce a range value;
   deriving an adjusted frequency value for each epoch based upon a ratio of the frequency difference value for that epoch and the range value; and
   providing the output as a function of the adjusted frequency values.

6. The method of claim 2 wherein providing the output as a function of the frequency difference values comprises:
   providing a plurality of graphical representations of a human subject's head, each graphic representation corresponding to one of the plurality of epochs; and
   providing an indicium associated with each graphical representation which is representative of a region from which the EEG signal is derived, the indicium having a characteristic which is a function of the frequency difference value for the epoch corresponding to the graphical representation.

7. The method of claim 6 wherein the characteristic of the indicia is a function of sign of the frequency difference value.

8. The method of claim 7 wherein the characteristic which is a function of the sign of the frequency difference value is a color of the indicium, and wherein the indicium has a first color representative of a positive frequency difference value and a second color representative of a negative frequency difference value.

9. The method of claim 6 wherein the characteristic of the indicium is a function of magnitude of the frequency difference value.

10. The method of claim 9 wherein providing the output further comprises:
    comparing a maximum and a minimum calculated frequency value from among the frequency values for the plurality of epochs to produce a range value;
    deriving an adjusted frequency value for each epoch based upon a ratio of the frequency difference value for that epoch and the range value; and
    wherein the indicium has an area which is a function of magnitude of the adjusted frequency value.

11. The method of claim 2 wherein each of a plurality of EEG signals derived from different sites are processed according to the method for each of the plurality of epochs to produce a frequency value and a frequency difference value for each site for each epoch.

12. The method of claim 11 wherein providing an output indicative of cerebral activity further comprises:
    comparing a maximum and a minimum calculated frequency value from among the frequency values for the plurality of epochs to produce a range value;
    deriving an adjusted frequency value for each epoch based upon a ratio of the frequency difference value for that epoch and the range value;
    comparing the adjusted frequency values of the sites for each epoch;
    providing an output representative of relative amounts of change in frequency at the different sites corresponding to the EEG signals for each of the epochs, based upon the comparing of adjusted frequency values.

13. The method of claim 1 and further comprising:
    multiplying the digitized waveforms by a window function prior to transforming.

14. A method of processing a time-varying analog biological signal to provide a frequency value for each of a plurality of epochs which have different time relationships to an event, the method comprising:
    digitizing the biological signal to produce digital sample values representative of amplitude of the biological signal as a function of time;
    providing for each epoch, a first digitized waveform based at least in part upon the digital sample values derived from the epoch and in part upon fill values, the first digitized waveform having a length which is longer than the epoch;
    producing a frequency spectrum for each epoch based at least in part upon the first digitized waveform containing digital sample values derived from that epoch, the frequency spectrum having a frequency content which is uniquely attributable to the digital sample values derived from the epoch; and
    deriving a frequency value for each epoch based upon the frequency spectrum corresponding to that epoch.

15. A method of processing a time-varying analog biological signal to provide an indication of biological activity in response to an event, the method comprising:
    digitizing the biological signal to produce digital sample values representative of amplitude of the biological signal as a function of time;
    providing a first non-averaged digitized waveform of a first length, the first digitized waveform including digital sample values derived from an epoch which has a time duration which is less than the first length and which has a time relationship to the event;
    providing a second non-averaged digitized waveform of a second length equal to the first length and partially overlapping in time with the first digitized waveform, but which does not include digital sample values derived from the epoch;
    transforming the first digitized waveform to a first frequency spectrum;
    transforming the second digitized waveform to a second frequency spectrum;
    producing a difference frequency spectrum representative of a difference between the first frequency spectrum and the second frequency spectrum;
    deriving a frequency value for the epoch based upon the difference frequency spectrum; and
    providing an output indicative of biological activity during the epoch based upon the frequency value for that epoch.

16. A method of processing an EEG signal, the method comprising:
    sampling the EEG signal during a time interval having a time relationship to an event to produce digital sample values representative of amplitude of the EEG signal as a function of time;

producing, for each of a plurality of epochs having different time relationships to the event, a frequency spectrum based upon a digitized waveform which covers a time period longer than the epoch and which has a frequency content which is uniquely attributable to the digital sample values derived from that epoch;

deriving, for each of the plurality of epochs, a frequency value based upon the frequency spectrum corresponding to that epoch; and providing an output as a function of the frequency values for the plurality of epochs.

17. A method of processing an EEG signal to provide an indication of cerebral activity in response to an event, the method comprising:

providing a plurality of tests which include:

sampling the EEG signal to produce digital sample values representative of amplitude of the EEG signal as a function of time;

providing first and second non-averaged digitized waveforms which are based at least in part upon the digital sample values and which represent first and second time intervals having essentially equal lengths but different time relationships to the event, wherein the first and second time intervals are staggered and are partially overlapping to define an epoch which has a time duration which is less than a the lengths of the first and second time intervals and which has a time relationship to the stimulus so that only one of the first and second time intervals includes digital sample values corresponding to the epoch;

transforming the first and second digitized waveforms from a time domain to a frequency domain to produce a first frequency spectrum and a second frequency spectrum representative of amplitude of the EEG signal at selected frequencies during the first and second time intervals, respectively;

subtracting the second frequency spectrum from the first frequency spectrum to produce a difference frequency spectrum which is a function of amplitude of the EEG signal at selected frequencies during the epoch;

deriving a frequency value for the epoch based upon the difference frequency spectrum;

averaging the frequency values for the epoch obtained from the plurality of tests to produce an averaged frequency value; and providing an indication of cerebral activity as a function of the averaged frequency value.

18. The method of claim 17 wherein the plurality of tests are performed for each of a plurality of different epochs, and wherein providing an indication of cerebral activity comprises:

comparing the averaged frequency value for each epoch with a reference frequency value to produce a frequency difference value for each epoch; and providing an output as a function of the frequency difference values for the plurality of epochs.

19. A system for processing an analog EEG signal, the system comprising:

means for producing a first non-averaged digitized waveform representative of amplitude of the EEG signal as a function of time during a first time interval;

means for producing a second non-averaged digitized waveform representative of amplitude of the EEG signal as a function of time during a second time interval, wherein the first and second intervals are essentially equal in length and staggered in time to define an overlapping portion when both intervals are occurring and a nonoverlapping portion in which only one of the intervals is occuring, the nonoverlapping portion having a time duration which is less than the length of the intervals;

means for transforming the first digitized waveform to a first frequency spectrum representative of amplitude of the EEG signal as a function of frequency of the EEG signal during the first time interval;

means for transforming the second digitized waveform to a second frequency spectrum representative of amplitude of the EEG signal as a function of frequency of the EEG signal during the second time interval;

means for subtracting the second frequency spectrum from the first frequency spectrum to produce a difference frequency spectrum representative of amplitude of the EEG signal as a function of frequency of the EEG signal during the nonoverlapping portion; and means for providing an indication of frequency response during the nonoverlapping portion based upon the difference frequency spectrum.

20. A system for processing EEG signals derived from a plurality of sites to provide an indication of cerebral activity as a function of time in response to a stimulus, the system comprising:

means for providing a stimulus during each of a plurality of tests;

analog-to-digital converter means for sampling each EEG signal;

storage means for storing digital sample values produced by the analog-to-digital converter means for each EEG signal, the digital sample values being representative of amplitude of the corresponding EEG signal as a function of time;

means for providing first and second non-averaged digitized waveforms, for each EEG signal and each test, which are based at least in part on the digital sample values and represent a first and a second time interval of essentially equal length, respectively, which define one of a plurality of epochs having different time relationships to the stimulus and a duration which is less than the lengths of the first and second time intervals, the first and second time intervals being staggered and partially overlapping and wherein the epoch is defined by presence of only one of the first and second time intervals;

means for transforming the first and second digitized waveforms for each EEG signal from a time domain to a frequency domain to produce a first and a second frequency spectrum, respectively;

means for subtracting the second frequency spectrum from the first frequency spectrum for each EEG signal to produce a difference frequency spectrum;

means for deriving a frequency value for each EEG signal during each of the plurality of epochs based upon a corresponding difference frequency spectrum; and means for providing an indication of cerebral activity at each of a plurality of sites from which the EEG signals are derived as a function of the frequency values.

21. A system for processing a time-varying analog biological signal to provide a frequency value for each of a plurality of epochs which have different time relationships to an event, the system comprising:
means for digitizing the biological signal to produce digital sample values representative of amplitude of the biological signal as a function of time;
means for providing, for each epoch, a non-averaged digitized waveform based at least in part upon the digital sample values from the epoch, the digitized waveform having a length which is greater than a length of the epoch;
means for producing a frequency spectrum for each epoch as a function of the digitized waveform for that epoch, the frequency spectrum having a frequency content which is uniquely attributable to the digital sample values from the epoch; and
means for deriving the frequency value for each epoch based upon the frequency spectrum corresponding to that epoch.

22. A system for processing an EEG signal, the method comprising:
means for sampling the EEG signal during a time interval having a time relationship to an event to produce digital sample values representative of amplitude of the EEG signal as a function of time;
means for producing, for each of a plurality of epochs having different time relationships to the event, a frequency spectrum based upon a digitized waveform which is longer than the epoch and which has a frequency content which is uniquely attributable to the digital sample values corresponding to that epoch;
means for deriving, for each of the plurality of epochs, a frequency value based upon the frequency spectrum corresponding to that epoch; and
means for providing an output as a function of the frequency values for the plurality of epochs.

23. A method of processing an EEG signal to provide an indication of cerebral activity during an epoch, the method comprising:
digitizing the EEG signal to produce digital sample values representative of amplitude of the EEG signal as a function of time, including at least one digital sample value representative of amplitude of the EEG signal during the epoch;
forming a digitized waveform having those digital sample values which are representative of amplitude of the EEG signal during the epoch located at its center and having fill values surrounding those digital sample values;
transforming the digitized waveform from a time domain to a frequency domain to produce a frequency spectrum; and
deriving a frequency value for the epoch based upon the frequency spectrum.

24. The method of claim 23, wherein forming a digitized waveform comprises:
selecting a plurality of digital sample values associated with the epoch;
multiplying the digital sample values by a window function; and
forming a digitized waveform in which the digital sample values, as multiplied by the window function, are surrounded at each end by a plurality of fill values.

* * * * *